(12) United States Patent
Stern

(10) Patent No.: US 7,153,673 B2
(45) Date of Patent: Dec. 26, 2006

(54) MICROFLUIDIC DEVICES AND METHODS FOR PERFORMING TEMPERATURE MEDIATED REACTIONS

(75) Inventor: Seth R. Stern, Mountain View, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 505 days.

(21) Appl. No.: 10/676,334

(22) Filed: Sep. 30, 2003

(65) Prior Publication Data

US 2004/0081997 A1   Apr. 29, 2004

Related U.S. Application Data

(62) Division of application No. 09/952,045, filed on Sep. 13, 2001, now Pat. No. 6,670,153.

(60) Provisional application No. 60/232,349, filed on Sep. 14, 2000.

(51) Int. Cl.
   *C12Q 1/68*   (2006.01)
   *C12P 19/34*   (2006.01)

(52) U.S. Cl. .......................... 435/91.2; 435/6

(58) Field of Classification Search .................. 435/6, 435/91.2
   See application file for complete search history.

(56) References Cited

U.S. PATENT DOCUMENTS

| | | |
|---|---|---|
| 5,176,203 A | 1/1993 | Larzul |
| 5,779,868 A | 7/1998 | Parce et al. |
| 5,858,195 A | 1/1999 | Ramsey |
| 5,863,502 A | 1/1999 | Southgate et al. |
| 5,942,443 A | 8/1999 | Parce et al. |
| 5,965,001 A | 10/1999 | Chow et al. |
| 5,965,410 A | 10/1999 | Chow et al. |
| 6,020,141 A | 2/2000 | Pantoliano et al. |
| 6,033,546 A | 3/2000 | Ramsey |
| 6,062,261 A | 5/2000 | Jacobson et al. |
| 6,103,537 A | 8/2000 | Ullman et al. |
| 6,221,600 B1 | 4/2001 | MacLeod |
| 6,300,075 B1 | 10/2001 | Preston et al. |
| 6,303,343 B1 | 10/2001 | Kopf-Sill |
| 6,537,799 B1 * | 3/2003 | Chow et al. ............. 435/285.2 |

FOREIGN PATENT DOCUMENTS

| | | |
|---|---|---|
| WO | WO-94/05414 | 3/1994 |
| WO | WO-96/04547 | 2/1996 |
| WO | WO-97/02357 | 1/1997 |
| WO | WO-98/00707 | 1/1998 |
| WO | WO-98/45481 | 10/1998 |

OTHER PUBLICATIONS

Chou, Q. et al., "Prevention of pre-PCR mis-priming and primer dimerization improves low-copy-number amplifications," Nucl. Acids Res. (1992) 20(7):1717-1723.
D'Aquila, R.T. et al., "Maximizing sensitivity and specificity of PCR by pre-amplification heating," Nucl. Acids Res. (1991) 19:3749.
Kainz, P. et al., "Specificity-Enhanced Hot-Start PCR: Addition of Double-Stranded DNA Fragments Adapted to the Annealing Temperature," BioTechniques (2000) 28(2):278-282.
Kaijalainen, S. et al., "An alternative hot start technique for PCR in small volumes using beads of wax-embedded reaction components dried in trehalose," Nucl. Acids Res. (1993) 21(12):2959-2960.
Kellogg, D.E. et al., "TaqStart Antibody: 'Hot Start' PCR Facilitated by a Neutralizing Monoclonal Antibody Directed Against Taq DNA Polymerase," BioTechniques (1994) 16(6):1134-1137.
Manz, A. et al., "Micromachining of monocrystalline silicon and glass for chemical analysis systems," Trends in Anal. Chem. (1991) 10(5):144-149.
Manz, A. et al., "Planar Chips Technology for Miniaturization of Separation Systems: A Developing Perspective in Chemical Monitoring," Adv. in Chromatog. (1993) 33:1-66.
Moretti, T. et al., "Enhancement of PCR Amplification Yield and Specificity Using AmpliTaq Gold DNA Polymerase," BioTechniques (1998) 25(4):716-722.

* cited by examiner

*Primary Examiner*—Kenneth R. Horlick
(74) *Attorney, Agent, or Firm*—Donald R. McKenna; Ann C. Petersen

(57) ABSTRACT

In a method for performing a hot start polymerase chain reaction, a reaction mixture including a primer, a template molecule, and a buffer—but no polymerase enzyme—is loaded in a reaction channel of a microfluidic device. An electrical current is applied to heat the reaction channel. A polymerase enzyme is delivered into the reaction channel, and the reaction channel is subjected to conditions such that the hot start polymerase chain reaction is performed. In a method for performing a temperature mediated reaction, a first component of the temperature mediated reaction is loaded in a reaction channel of a microfluidic device. An electrical current is applied to heat the reaction channel. A second component of the temperature mediated reaction is delivered into the reaction channel, and the reaction channel is subjected to conditions such that the temperature mediated reaction is performed.

13 Claims, 6 Drawing Sheets

MICROFLUIDIC DEVICES AND METHODS FOR PERFORMING TEMPERATURE MEDIATED REACTIONS

CROSS REFERENCE TO RELATED APPLICATION

This application is a divisional of U.S. patent application 09/952,045, filed Sep. 13, 2001, now U.S. Pat. No. 6,670,153, which claims priority to Provisional Patent Application No. 60/232,349, filed Sep. 14, 2000, each of which is incorporated herein by reference in its entirety for all purposes.

BACKGROUND OF THE INVENTION

There has been a growing interest in the manufacture and use of microfluidic systems for the acquisition of chemical and biochemical information. Techniques commonly associated with the semiconductor electronics industry such as photolithography, wet chemical etching, etc., are being used in the fabrication of these microfluidic systems. The term "microfluidic", refers to a system or device or "chip" having channels and chambers which are generally fabricated at the micron or submicron scale, e.g., having at least once cross-sectional dimension in the range of from about 0.1 µm to about 500 µm. Early discussion of the use of planar chip technology for the fabrication of microfluidic systems is provided in Manz et al., *Trends in Anal. Chem.* (1990) 10(5):144–149 and Manz et al., *Adv. in Chromatog.* (1993) 33:1–66, which describe the fabrication of such fluidic devices, and particularly microcapillary devices, in silicon and glass substrates.

Applications of microfluidic systems are myriad. For example, International Patent Appln. WO 96/04547 describes the use of microfluidic systems for capillary electrophoresis, liquid chromatography, flow injection analysis, and chemical reaction and synthesis. U.S. Pat. No. 5,942,443 entitled "HIGH THROUGHPUT SCREENING ASSAY SYSTEMS IN MICROFLUIDIC DEVICES", issued on Aug. 24, 1999 discloses wide ranging applications of microfluidic systems in rapidly assaying large numbers of compounds for their effects on chemical, and preferably biochemical systems. Biochemical systems include the full range of catabolic and anabolic reactions which occur in living systems including enzymatic, binding, signaling and other reactions. Biochemical systems of particular interest include receptor-ligand interactions, enzyme-substrate interactions, cellular signaling pathways, transport reactions involving model barrier systems (e.g., cells or membrane fractions) for bio-availability screening, and a variety of other general systems.

One of the major advances in recent times has been the adaptation of microfluidic devices to the performance of the polymerase chain reaction (PCR) and other cyclic polymerase-mediated reactions. However, a significant problem faced by experimenters has been the control of process parameters such as temperature, reagent concentration, buffers, salts, other materials, and the like. In particular, PCR should be carried out at precisely controlled temperatures. For example, PCR is typically based on three discrete, multiply repeated steps: denaturation of a DNA template, annealing of a primer to the denatured DNA template, and extension of the primer with a polymerase to create a nucleic acid complementary to the template. The conditions under which these steps are performed are well established in the art. Each step has distinct temperature and time requirements typically as follows:

| | |
|---|---|
| Denaturation | 96° C., 15 seconds |
| Primer Annealing | 55° C., 30 seconds |
| Primer Extension | 72° C., 1.5 minutes |

See Innis et al., *PCR Protocols: A Guide to Methods and Applications* (Academic Press, Inc.;1990). Generally, microfluidic systems are well suited to the performance of PCR because they allow rapid temperature changes, quickly providing the correct temperature at each step. Further, because the microfluidic elements are extremely small in comparison to the mass of the substrate in which they are fabricated, the heat can be highly localized, e.g., it dissipates into and from the substrate before it affects other fluidic elements within the device.

In addition to efficient temperature control, an experimenter attempting to run PCR must overcome a second problem. Often the efficiency of amplification reactions is compromised by primer self-annealing ("primer dimer") as well as larger non specific side-reaction products arising due to inefficient reaction conditions. Such nonspecific fragments adversely affect the yield of desired specific fragments through competition with the specific target in the reaction. Furthermore, the nonspecific fragments that are approximately the same size as the specific product can cause erroneous interpretation of results. Researchers have concluded that these nonspecific side reaction products originate from DNA polymerase catalyzed extension of partially annealed 3' ends of primers to nonspecific sites in complex DNA under ambient temperature conditions. Therefore, it appears that efficiencies of thermostable DNA polymerases are greatly reduced at ambient temperature relative to their peak efficiencies at higher temperatures.

A "Hot Start" PCR method was developed as a means of reducing the amplification of nonspecific products. See, e.g., D'Aquila et al., (1991) *Nucleic Acids Res*. 19:37–49. In the earlier methods, one of the reaction components was withheld from the reaction until the reaction mixture was heated to a temperature greater than the annealing temperature, followed by the addition of the missing component. This approach causes the partially annealed 3' primer ends to melt away from nonspecific sites, before they can be extended. Therefore, Hot Start PCR improves product yield and specificity. More recent approaches to "Hot Start" PCR include the use of a heat-labile wax or jelly barrier that melts and permits mixing of aqueous components at an elevated temperature. Chou et al., (1992) *Nucleic Acids Res*, 20:1717–1723. A third method utilizes a monoclonal antibody for deactivating Taq DNA Polymerase at ambient temperature. When the reaction mixture is heated to the denaturation temperature, the deactivation of the polymerase is reversed thereby facilitating amplification of specific targets. Kellogg et al., (1994) *Biotechniques* 16: 1134–1137. Although all of the above described methods are a significant improvement over simple PCR, a common problem associated with all these methods is that these methods are cumbersome to use and time consuming when working with multiple samples.

For the foregoing reasons, there is a need for efficient methods, devices and systems for performing temperature dependent reactions, such as hot start PCR, on multiple sample targets. The present invention satisfies this and other needs.

BRIEF SUMMARY OF THE INVENTION

The present invention is directed to microfluidic systems including methods and devices for performing temperature mediated reactions in a precise and efficient manner.

Generally, the present invention is directed to microfluidic devices and methods of using the same, wherein the devices incorporate improved channel and reservoir configurations such that reaction components of a temperature mediated reaction are heated in a region of the device, while additional reaction components are added into the heated reaction mixture from a separate source, e.g., through a side channel.

In a first aspect, the present invention provides a microfluidic device that comprises a body structure having at least one microchannel with a heating region. A plurality of electrical access channels having first and second ends intersect the at least one microchannel at the first end. The electrical access channels are in fluid communication with partially filled reservoirs at the second end.

In a related aspect, the present invention provides a microfluidic device that comprises a body structure having a microchannel with a heating region, wherein the heating region has a first reaction component or components disposed in it but not a second reaction component. The heating region of the microchannel has a first electrical resistance. Two electrical access channels having a second electrical resistance, which is lower than the first electrical resistance, are in fluid communication with the microchannel. A source of a second reaction component is in fluid communication and intersects the heating region of the microchannel at a first intersection. The electrical access channels intersect the reaction channel on different sides of the first intersection. For example, in a device used for Hot Start PCR, the heating region of the device has primers but no polymerase disposed in it and the polymerase enzyme is introduced into the reaction mixture via a side channel which intersects the microchannel at a first intersection.

In another aspect, the present invention provides a microfluidic device described above, but comprising a source of reaction mixture slugs, in fluid communication with the reaction channel.

In a yet another aspect, the present invention employs a material transport system for delivering the polymerase enzyme and the reaction mixture into the reaction channel.

The present invention also provides methods for performing temperature mediated reactions using the devices described herein, which method comprises loading a first component of a temperature mediated reaction in a heating region of the reaction channel of the device, wherein the reaction channel is heated by applying an electrical current and subsequently delivering a second component of the temperature mediated reaction into the reaction channel.

In a related aspect, the present invention also provides methods of performing a temperature mediated reaction as described above, on a series of reaction mixture slugs where the reaction mixture comprises a first component of the temperature mediated reaction.

DETAILED DESCRIPTION

I. General

Figure 1:
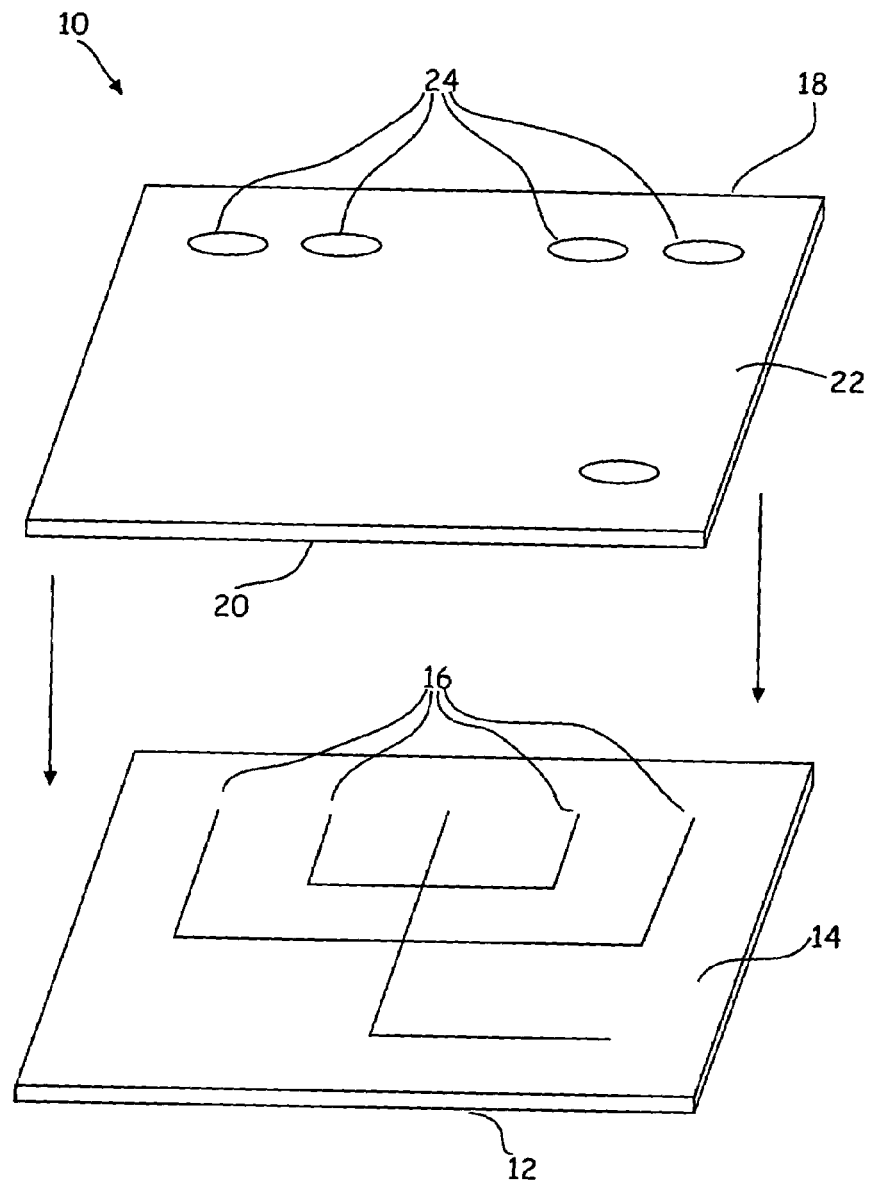
FIG. 1 illustrates a simplified diagram of a microfluidic device.

The present invention generally provides microfluidic systems including devices incorporating improved channel configuration and a reaction channel, as well as methods for using these devices for performing temperature mediated reactions on multiple samples with ease of use and efficient consumption of resources. In general, the present invention provides devices, systems and methods of using same for performing temperature mediated reactions by providing a reaction mixture at an elevated temperature, e.g., a temperature optimal or advantageous to a desired reaction. One or more additional reactants are added to the heated reaction mixture to allow immediate initiation of the desired reaction. Examples of such reactions include cyclic polymerase reactions such as PCR, Temperature dependent protein binding assays, and the like. In carrying out described methods, the present invention also provides novel devices, e.g. microfluidic devices, having improved channel and reservoir configurations and systems incorporating such devices. In particular, the invention provides microfluidic devices incorporating improved channel and reservoir configurations that facilitate electrical conductivity through fluidic components disposed within the channels of the devices, while preferably restricting fluid flow from the reservoirs into the reaction channel.

A typical technique for performing a temperature mediated reaction using the devices of the present invention is outlined as follows:

1. Provide a first component of a temperature mediated reaction into the reaction channel of the device.
2. Elevate the temperature in a region of the reaction channel to a first temperature.
3. Deliver a second component into the reaction channel so as to mix with the first component.
4. Cycle the temperature of the reaction mixture to a second temperature. OR
5. Hold the temperature in the reaction channel steady at the first temperature.

The phrase "biochemical system" generally refers to a chemical interaction which involves molecules of the type found specifically within living organisms.

A "temperature mediated reaction" refers to a chemical or biochemical reaction wherein the reactivity of some of the components is temperature dependent e.g., increase or decreased by elevated temperature.

A "thermocyclic reaction" is a multi-step reaction wherein at least two steps are carried out at different temperatures.

"PCR" refers to a polymerase chain reaction, which is a thermocyclic, polymerase-mediated, DNA amplification reaction. A PCR typically includes template molecules, oligonucleotide primers complementary to each strand of the template molecules, a thermostable DNA polymerase, and deoxyribonucleotides, and involves three distinct processes that are multiply repeated to effect the amplification of the original nucleic acid. The three processes (denaturation, hybridization, and primer extension) are performed at 2 or 3 distinct temperatures and temporal steps.

"Hot Start" PCR refers to preheating a PCR reaction mixture to a desired reaction temperature prior to the addition of a reagent required for the reaction, typically this would mean mixing the polymerase with reaction components only after the reaction mixture is heated, this minimizes extension of misprimed or misannealed reaction components.

A "template molecule" refers to a molecule of specific identity which can serve as a template for the synthesis of a complementary molecule. Most often, a "template molecule" is a polymeric molecule. In the context of "PCR", a "template molecule" may represent a fragment or fraction of the nucleic acids added to the reaction. Specifically, a "template molecule" refers to the sequence between and including the two primers.

A "polymerase" is an enzyme that catalyzes the sequential addition of monomeric units to a polymeric chain, or links two or more monomeric units to initiate a polymeric chain. In preferred embodiments of this invention, the "polymerase" will work by adding monomeric units whose identity is determined by and which is complementary to a template molecule of a specific sequence. For example, DNA polymerases such as DNA pol 1 and Taq polymerase add deoxyribonucleotides to the 3' end of a polynucleotide chain in a template-dependent manner, thereby synthesizing a nucleic acid that is complimentary to the template molecule.

"Denaturation" of a target molecule refers to the unfolding or other structural alteration of the target. For example, denaturation of a protein refers to the removal of secondary, tertiary or quaternary structure. In the case of nucleic acids, a denatured nucleic acid is one which has been modified to unfolded, uncoiled, untwisted or single stranded form. Specifically, in case of DNA, "denaturation" refers to the separation of the two complementary strands of the double helix, thereby creating two complementary, single stranded template molecules.

"Hybridization" of two nucleic acids refers to the binding of two complementary single stranded nucleic acids to form a double-stranded nucleic acid.

The "extension of the primer molecules" refers to the addition of nucleotides to a primer molecule so as to synthesize a nucleic acid complementary to a template molecule.

A "reaction mixture slug" as used herein is a discrete fluid region, typically in a microscale channel, which comprises a reaction mixture including one or more components of a chemical or biochemical reaction. In accordance with the invention, the reaction mixture slugs may lack a second component whose reactivity with the desired components of the reaction mixture is temperature dependent. In the context of PCR, a "reaction mixture slug" may comprise primers, template molecules, buffers, nucleotides but lack the DNA polymerase.

II. Microfluidic Devices Incorporating Improved Reservoir Configurations:

In accordance with at least a first aspect, the invention provides microfluidic devices that incorporate unique channel and reservoir configurations so as to facilitate electrical conductivity through fluids contained in the channels while restricting the migration of these fluids from electrode channels into a reaction channel. The microfluidic devices of the present invention comprise a central body structure in which the various microfluidic elements are disposed. For example, the body structures of the microfluidic devices of the present invention typically employ a solid or semi-solid substrate that is typically planar in structure, i.e., substantially flat or having at least one flat surface.

The channels and/or chambers of the microfluidic devices are typically fabricated into the upper surface of the bottom substrate or portion 12, as microscale grooves or indentations 16, using the above described microfabrication techniques. The top portion or substrate 18 also comprises a first planar surface 20, and a second surface 22 opposite the first planar surface 20. In the microfluidic devices prepared in accordance with the methods described herein, the top portion also includes a plurality of apertures, holes or ports 24 disposed therethrough, e.g., from the first planar surface 20 to the second surface 22 opposite the first planar surface. (See FIG. 1).

The first planar surface 20 of the top substrate 18 is then mated, e.g., placed into contact with, and bonded to the planar surface 14 of the bottom substrate 12, covering and sealing the grooves and/or indentations 16 in the surface of the bottom substrate, to form the channels and/or chambers (i.e., the interior portion) of the device and are oriented such that they are in communication with at least one of the channels and/or chambers formed in the interior portion of the device from the grooves or indentations in the bottom substrate. In the completed device, these holes function as reservoirs for facilitating fluid or material introduction into the channels or chambers of the interior portion of the device, as well as providing ports at which electrodes may be placed into contact with fluids within the device, allowing conduction of electrical current along the channels of the device to controllably heat and direct fluid transport within the device.

Although described in terms of fabricating channels in one substrate and reservoirs in the other, it will be appreciated that both may be fabricated in a single substrate with a plain substrate layer overlaying and sealing the channels.

Suitable substrates may be fabricated from any one of a variety of materials, or combinations of materials. Often, substrates are manufactured using solid substrates common in the fields of microfabrication, e.g., silica, silicon or gallium arsenide. In the case of these substrates, common microfabrication techniques, such as photolithographic techniques, wet chemical etching, micromachining, i.e., drilling, milling and the like, may be readily applied in the fabrication of microfluidic devices and substrates. Alternatively, polymeric substrate materials may be used to fabricate the devices of the present invention, including, e.g. polydimethylsiloxanes (PDMS), polymethylmethacrylate (PMMA), polyurethane, polyvinylchloride (PVC), polystyrene, polysulfone, polycarbonate and the like. In the case of such polymeric materials, injection molding or embossing methods may be used to form the substrates having the channel dimensions and configuration as described herein.

Figure 3:
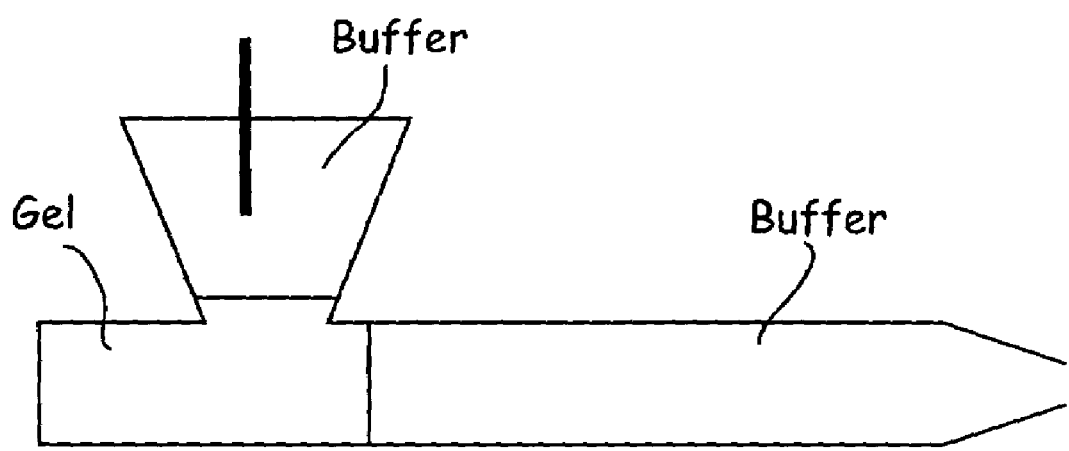
FIG. 3 illustrates plugged reservoirs for prevention of fluid flow.

In one aspect, the devices of the present invention comprise a horizontal microchannel comprising a heating region. Large electrical access channels intersect and are in fluid communication with the horizontal microchannel at first and second intersections, respectively. The region of the microchannel between the first and second intersections constitutes a heating region. In some embodiments, the ratio of the cross-sectional area of the microchannel to the large electrical access channels is 1:2. Preferably, this ratio is 1:5. More preferably, this ratio is 1:10. By virtue of the structural features of the channels, the devices would normally have low resistance paths for both fluid flow and electrical current flow. However, one aspect of this invention is the ability to locally heat fluid components within the heating region of the microchannel by applying an electrical current through the fluid components, while simultaneously preventing fluid flow from the electrical access channels into the microchannel. This is optionally accomplished by creating high fluidic resistance within the electrical access channels. In one particular example, the opposite ends of the electrical access channels are in fluid communication with reagent wells or reservoirs. An electrically conducting gel is introduced into the bottom of the reservoir. This is conveniently accomplished by adding a polyacrylamide gel matrix to the reservoir in liquid form and subsequently polymerizing it to form a conformably fitting gel barrier to fluid flow. The polymerized gel is then overlayed with buffer. Electrodes are disposed within each of the reagent wells or reservoirs. An energy source is operably coupled to the reservoirs for elevating the temperature of the fluid components in the horizontal channel. (See FIG. 3).

A variety of other methods and configurations are available for preventing fluid flow in access channels including fabricating channels with sufficiently high flow resistance, e.g., narrower or shallower channels, or incorporating various barriers, e.g., frits, and the like.

III. Microfluidic Devices for Performing Hot Start PCR:

The microfluidic devices and methods of the invention are particularly useful in performing temperature mediated reactions for e.g., Hot Start PCR. Hot Start PCR is a cyclic polymerase reaction wherein one of the reaction components of PCR is withheld until the reaction mixture comprising the remaining components is heated to a desired temperature. Typically, the DNA polymerase is withheld and added into the reaction mixture after the temperature has reached the desired temperature, thereby, minimizing the formation of nonspecific PCR products due to mispriming and primer oligomerization. The novel channel and reservoir configurations of the microfluidic devices of this invention have enabled the use of these devices for performing "hot start" PCR on multiple targets with ease of use and efficiency.

Generally, the devices of the present invention comprise a heating region having PCR reaction components other than the polymerase disposed in it. A source of the polymerase is in fluid communication with the heating region. The polymerase is diluted into the preheated reaction components thereby preventing the formation of undesired side reaction products due to mispriming or oligomerization. The temperature in the heating region is varied cyclically for repeated cycles of denaturation, annealing and extension of the target molecules.

More particularly, in the microfluidic devices described herein, at least one microchannel also termed a reaction channel or a heating channel, is disposed in the substrate wherein PCR reaction components other than polymerase, are added and heated. Two or more large channels having an electrical resistance lower than the electrical resistance of the reaction channel, are fluidly connected with and intersect the reaction channel. A transverse channel for delivering polymerase into the heating region of the reaction channel is situated such that it intersects the reaction channel at a point in between the intersections of the large channels with the reaction channel. A sample loading source is fluidly connected to the reaction channel. The reaction mixture slugs are sequentially introduced into the reaction channel through the sample loading source. Typically, the sample source may comprise a pipettor fluidly connected to the reaction channel at one end and to a source of reaction mixture slugs, e.g., a well or wells of a multiwell plate at an opposite end. Alternatively, the sample loading source may be integrated into the device, e.g., as a well or plurality of wells disposed within the device and in fluid communication with the reaction channel.

Optionally, the devices of the present invention may comprise a plurality of reaction channels whereby a reaction mixture is split into several smaller slugs, each of which is diverted into a separate reaction channel. In these devices, a plurality of electrical access channels may be present in order to provide a heating region in each of the reaction channels. In certain embodiments, the microchannel networks of the device includes a plurality of parallel reaction channels and the methods additionally include flowing the reaction mixture slugs from a sample loading source into the plurality of parallel channels or into one or more ports in fluid communication with the plurality of parallel reaction channels. For example, the plurality of parallel reaction channels optionally include at least 6, 12, 24, 48, 96 or more parallel microchannels. The methods also include providing PCR reaction components in each of the reaction channels and simultaneously flowing the polymerase from at least one side channel into the heating region of each of the reaction channels. Simultaneous reactions of mixtures in parallel channels are described, for example, in co-owned pending application No. 60/283,527, filed Apr. 12, 2001 which is incorporated herein by reference in its entirety for all purposes.

The reaction mixture slugs including, e.g., template molecules, buffer, primer molecules, and nucleotides, are transported into the reaction channel from the respective sources. The temperature of the heating region of the reaction channel is continuously varied in a cyclical manner to accomplish thermal cycling of the reactants in the reaction mixture. Initially, upon transportation into the reaction channel, the reaction mixture is heated such that the target molecules contained in the reaction mixture undergo denaturation. DNA polymerase is diluted into the reaction channel from the transverse channel where it mixes with the reaction mixture. Thermal cycling within the reaction channel, including two or three distinct temperature periods, allows the reaction to proceed through the steps of denaturation, annealing and extension as described above. Typically, three distinct temperature periods corresponding to the denaturation, annealing and extension steps include a first period of about 95° C., a second period of about 50° C. to 65° C., and a third period of about 72° C. respectively. The cycle of denaturation, annealing and extension is repeated several times resulting in desired product yield of the target. Transportation of the reactants into and along the reaction channel may be accomplished by a number of ways including electrophoretic transport, electroosmotic flow or pressure based flow. The reaction channel is fabricated to transport the reagents out of the body after the last cycle is completed, whereupon the reagents or products can be collected for detection. Alternatively, reagents or products can be detected directly in the channel.

A technique for hot start PCR for multiple target molecules according to the present invention may briefly be outlined as follows:

(1) Provide a reaction mixture slug into the reaction channel;

(2) Apply an electric current to the fluid to increase temperature of reaction components to a first temperature;

(3) Deliver the DNA polymerase via the transverse channel into the heating region of the reaction channel;

(4) Remove electric current from fluid to decrease temperature of reaction components and products to second temperature; and (5) Apply an electric current to increase temperature of reaction components to a $3^{rd}$ temperature;

(6) Repeat steps 2, 4 and 5 successively until complete.

A. Improved Channel Configurations:

As noted above, the devices of this invention are used to perform Hot Start PCR by isolating a required reagent, e.g., DNA polymerase from the reaction mixture until the reaction mixture is heated to a high temperature so as to avoid the formation of non-specific side reaction products due to mispriming. Therefore, the devices of the present invention employ channel configurations designed to isolate the polymerase while maintaining fluid communication between the various channels. In particular, the system comprises a substrate having at least a first microscale channel disposed therein, the channel having a heating region. Fluidic reaction components are predisposed in the heating region of the microscale channel. A plurality of large channels having a cross sectional area significantly larger than the cross sectional area of the first microscale channel are fluidly connected to the microscale channel on either side of the heating region of the channel. The opposite termini of each of these large channels are in fluid communication with reagent wells or reservoirs. Electrodes are also typically disposed within each of the reagent wells or reservoirs.

An energy source is operably coupled to the reagent wells or reservoirs for elevating the temperature of the reaction components in the heating region of the channel by applying a first electrical current through the channel. The narrower cross-section of the microchannel provides higher electrical resistance in the fluid components which increases the temperature of the fluid as current passes therethrough. A sensor is optionally coupled to the channel to detect the temperature of the reaction components within the heating region of the microchannel. The temperature may be detected via the conductivity of the fluid. The measured fluid conductivity is correlated to the fluid temperature. The measured temperature is compared to a desired set-point. A controller coupled to the sensor and the energy source controls the temperature in the microchannel based upon a desired set point temperature.

Figure 2:
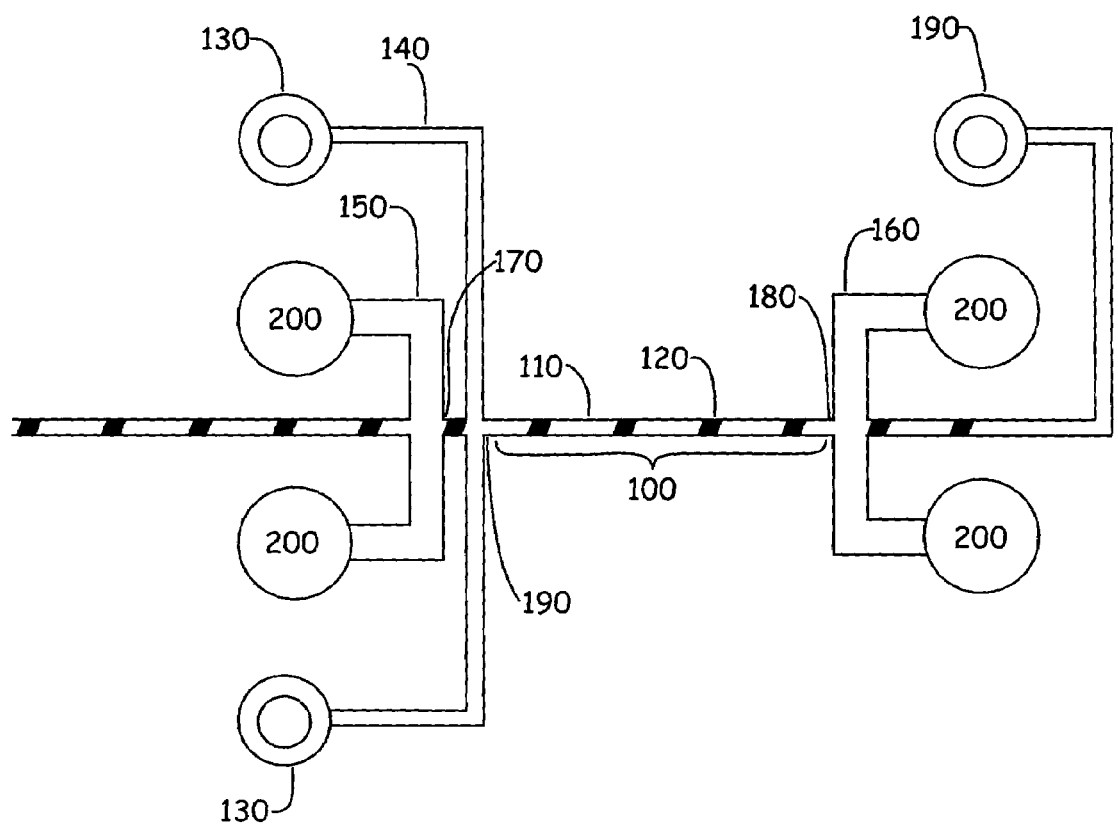
FIG. 2 illustrates the improved channel configurations employed in the devices of the present invention and their operation in a temperature mediated reaction.

FIG. 2 illustrates one embodiment of the devices of the present invention. As shown, the reaction channel 110 intersects and is in fluid communication with two large electrical access channels, 150 and 160 respectively, at intersections 170 and 180. A transverse channel 140, for introducing polymerase, is in fluid communication with the reaction channel 110 and intersects it at intersection 190. The electrical access channels 150 and 160 are in fluid communication with filled reservoirs 200, and flow an electrical current into the reaction channel between the intersections 170 and 180. Each of the reservoirs 200 is partially filled with a matrix. The electrical resistance of the electrical access channels 150 and 160 is less than the electrical resistance of the reaction channel 110. The heating region of the reaction channel is defined by intersections 170 and 180, and is typically 20 mm long and 15 μm deep. The reaction mixture slugs are introduced into the reaction channel via a sample loading source. Upon entering the heating region 100, each reaction mixture slug undergoes a series of amplification cycles as it travels through the region.

B. Source of Reaction Mixture

The reaction mixture slugs containing for example, PCR reaction components other than the DNA polymerase, can be loaded into the microchannel of the devices by placing the reaction mixture in a well fluidly connected to the microchannel. The reaction mixture is then flowed through the microchannel, e.g., by pressure or by electrokinesis.

Alternatively, reaction mixtures can be stored external to the microfluidic device in a system of wells, plates, or even as dried components stored on a surface. Pressure based pipettors or electropipettors can be used to access the reaction mixtures, or to re-hydrate soluble or suspendable dried components from dry storage media. An example of electropipettor is described in e.g., U.S. Pat. No. 5,779,868 and is incorporated herein by reference in its entirety for all purposes. A variety of access systems for coupling reagent storage and microfluidic systems are also described in Knapp et al. "Closed Loop Biochemical Analyzers" WO 98/45481.

IV. Temperature Control in the Microchannel

Controlled heating of the fluid in the heating region of the reaction channel can be accomplished in a number of ways. In a preferred embodiment, thermocycling for PCR and other thermocyclic applications can be conducted using joule heating. See, e.g. U.S. Pat. No. 5,965,410 and hereby incorporated by reference in its entirety for all purposes. In brief, an energy source is used to pass electrical current through fluid components that are disposed within the heating region of the reaction channel, for heating those components in a controlled, localized manner, i.e., localized within the reactants. This is particularly useful during PCR where the reaction mixture is heated in a thermocyclic fashion spanning the different degrees of temperature required for denaturation, annealing and extension, respectively. To selectively control the temperature of the fluid in the heating region of the microchannel, the energy source applies electrical current into the heating region of the microchannel. In preferred aspects, AC current, voltage, and/or frequency can be adjusted, for example, to heat the fluid with or without fluid movement. Alternatively, the energy source applies a pulse or impulse of current and/or voltage, which passes through the heating region of the microchannel to heat fluid at a given instance in time. In embodiments using electrokinetic fluid movement, the energy source may apply direct current (DC) to the microchannel via the large channels. This DC current can be selectively adjusted in magnitude to complement any voltage or electric field that may be applied to the microchannel to move materials in and out of the heating region of the microchannel.

In general, electrical current passing through the fluid in a channel produces heat by dissipating energy through the electrical resistance of the fluid. Power dissipates as the current passes through the fluid and goes into the fluid as energy as a function of time to heat the fluid. The following mathematical expression generally describes a relationship between power, electrical current, and fluid resistance. i.e., $$P=I^2R$$

Where, P=power dissipated in fluid

I=electric current passing through the fluid, and

R=electrical resistance of fluid.

In a preferred embodiment of the present invention, the heating region of the reaction channel is in fluid communication with large electrical access channels. The cross sectional area of the reaction channel is smaller than the cross sectional area of the electrical access channels. In some embodiments, the ratio of the cross sectional area of the reaction channel to the electrical access channels is at least 1:2. Preferably, this ratio of the cross sectional areas is at least 1:5. More preferably, the ratio of the cross sectional areas of the reaction channel to the electrical access channels is at least 1:10. Therefore, heating of the reaction components is easily accomplished because the smaller cross-section of the reaction channel provides higher resistance, which increases the power dissipated into the fluid as electric current passes through thereby increasing the temperature of the fluid. Alternatively, the electric current is increased across the length of the channel by increased voltage, which also increases the amount of power dissipated into the fluid to correspondingly increase the fluid temperature.

Figure 4:
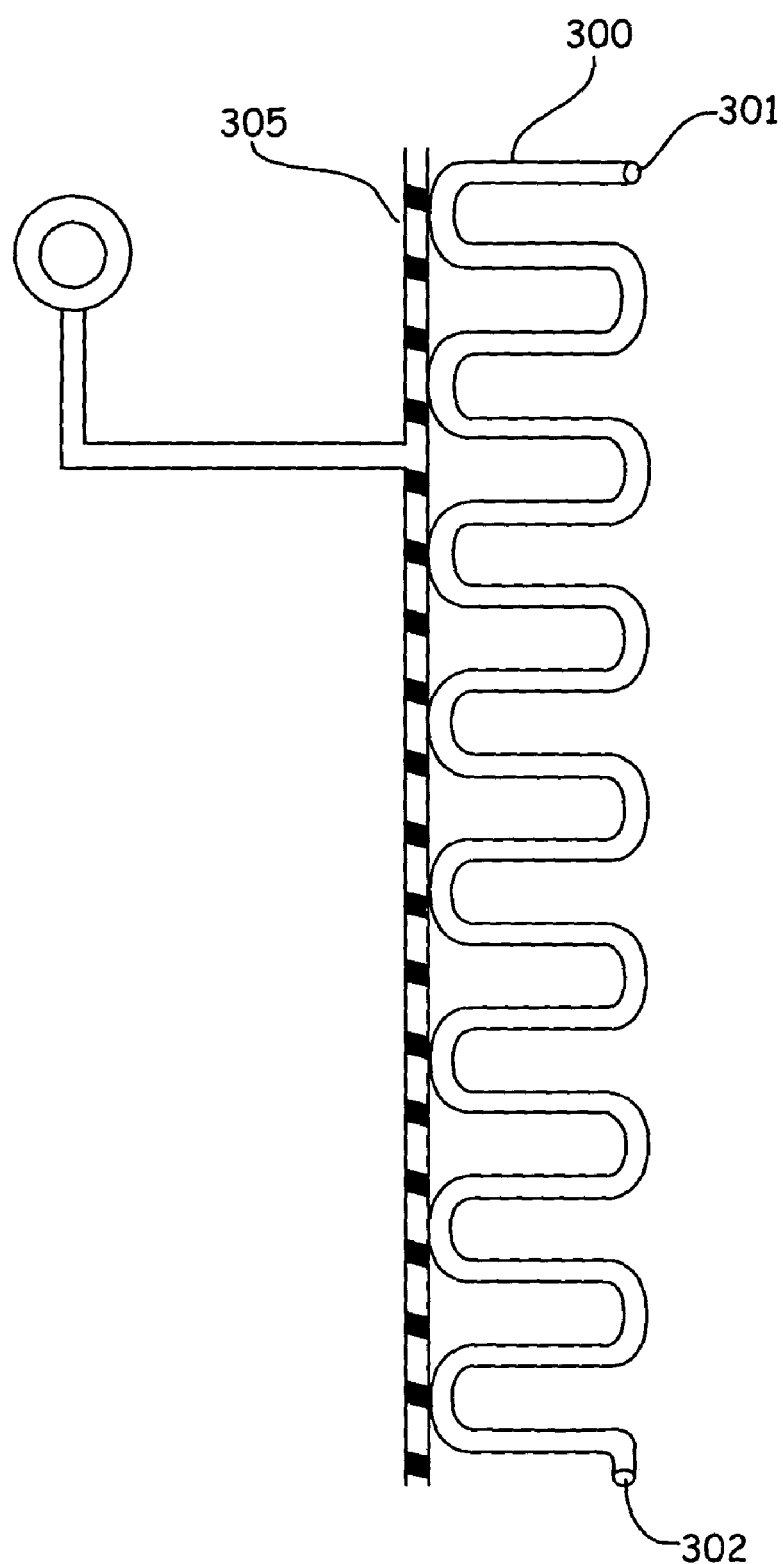
FIG. 4 illustrates a simplified diagram of a microfluidic device with a heating and cooling coil for thermal cycling according to the present invention.

In alternate embodiments, temperature cycling of the fluid components may be achieved by way of conduction, e.g. from heating and cooling coils incorporated on chips or external heating/cooling elements. As illustrated in FIG. 4, a heating coil 300 provides high temperature fluid from region 301 to 302, or in the inverse direction. The heating coil will typically be disposed adjacent to or in a layer above or below the region of the microchannel wherein heating of the fluid reactants is desired. Thermal energy is conducted through the substrate to the microchannel. Preferably, a power source supplies a voltage differential between the two ends of the coil, 301 and 302. The voltage differential is applied to the fluid using a pair of electrodes in contact with fluid in the coil in regions 301 and 302. The heated fluid through the coil 300 transfers thermal energy via a temperature gradient to fluid in the microchannel 305. Coil 300 is preferably close enough to or in contact with the microchannel 305 to transfer thermal energy from fluid in the coil to the fluid in the microchannel 305. The fluid in the coil can be moved using a variety of techniques as described above.

Cooling of the reaction mixture is achieved either through use of cooling fluid that travels through a coil to carry away thermal energy in the form of heat from the fluid in the microchannel 305, or by allowing rapid heat dissipation that is available in microfluidic systems. Heat from the fluid in the microchannel is removed using a combination of conduction and convection if necessary.

A controller or computer such as a personal computer, monitors the temperature of the fluid in the heating region of the microchannel. The controller or computer receives current and voltage information from, for example the energy source and identifies or detects temperature of fluid in the heating region. Depending upon the desired temperature of fluid in the heating region, the controller or computer adjusts voltage and/or current to meet the desired fluid temperature in a manner that is responsive to the temperature sensed within the channel by a temperature sensor.

V. Material Transport in the Microchannels

The control and transport of fluids in the microfluidic devices of the present invention may be accomplished by a variety of controlling instrumentation. For example, in many cases, fluid transport and direction may be controlled in whole or in part, using pressure based flow systems that incorporate external or internal pressure sources to drive fluid flow. Internal sources include microfabricated pumps, e.g., diaphragm pumps, thermal pumps, and the like that have been described in the art. See e.g., U.S. Pat. Nos. 5,271,724, 5,277,556, and 5,375,979 and Published PCT Application Nos. WO 94/05414 and WO 97/02357. The devices described herein can also utilize electrokinetic material direction and transport systems. Preferably, external pressure sources are used, and applied to ports in the devices that are disposed at channel termini. Single or multi port pressure sources are preferred. Typically, the pressure source is a vacuum source applied at the downstream terminus of the main channel. These applied pressures, or vacuums, generate pressure differentials across the lengths of channels to drive fluid flow through them. In the interconnected channel networks described herein, differential flow rates on volumes are optionally accomplished by applying different pressures or vacuums at multiple ports. Multi-port and single-port pressure systems are described in U.S. Ser. No. 60/184,390, filed Feb. 23, 2000 and in 60/159,014 filed Oct. 2, 1999, respectively, the disclosures of which are hereby incorporated herein by reference in their entirety for all purposes.

Figure 5:
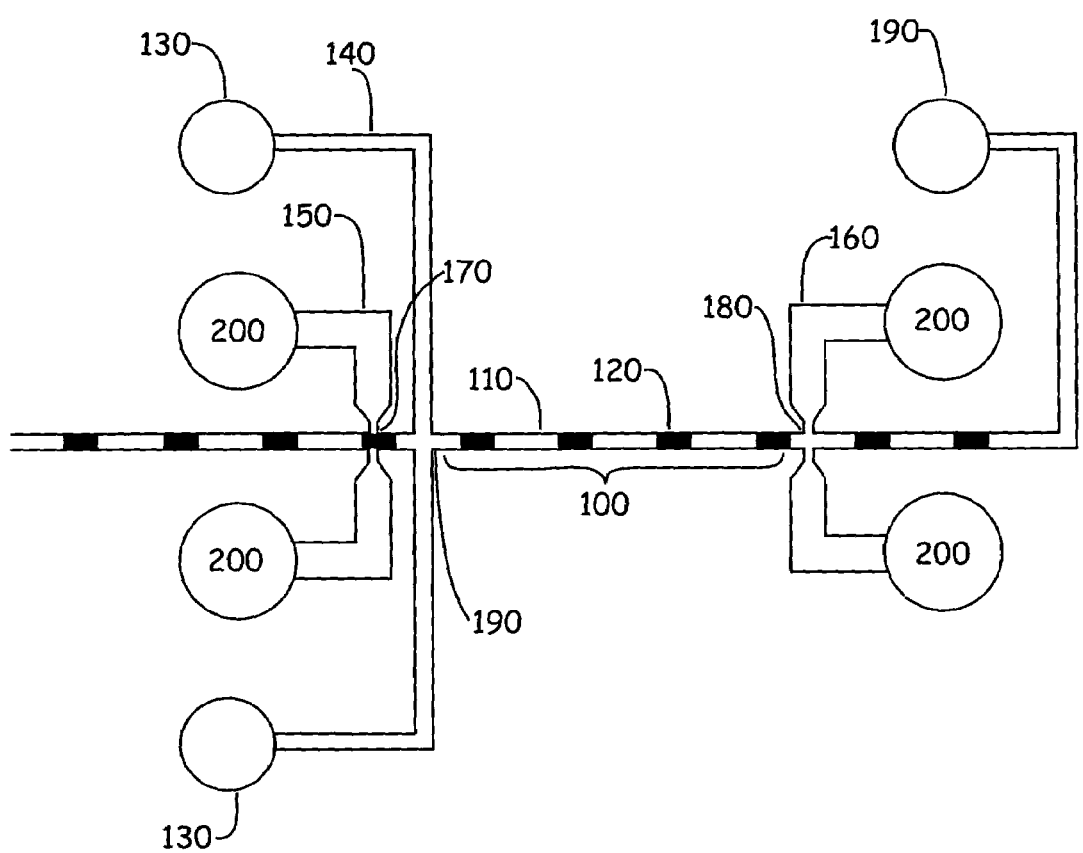
FIG. 5 illustrates microfluidic devices of the present invention incorporating narrow channel regions for preventing fluid diffusion.

One of the objectives of the devices of the present invention, is to enable fluid flow in the reaction channel so as to transport reaction mixture slugs and DNA polymerase into and through the reaction channel while restricting the flow of the fluid from the electrode channels into the reaction channel. In devices incorporating pressure based flow, one of the ways of accomplishing this is by partially filling the reservoirs at the opposite termini of the large channels with a gel matrix. Alternatively, the electrode channels are configured to have a necking down of the channel cross section in the regions intersecting the reaction channel so as to minimize diffusive effects. (See FIG. 5).

Although the devices have been described as utilizing a pressure based material transport system it will be appreciated that the devices described herein may utilize electrokinetic material direction and transport systems. "Electrokinetic material transport systems" as used herein, include systems that transport and direct materials within a microchannel through the application of electrical fields to the materials, thereby causing material movement through and along the channel. In particular, the preferred microfluidic devices described herein, include a body structure which includes at least three intersecting channels, which channels include at least four unintersected termini. It is desirable to have material flow through the heating region of the reaction channel e.g., from left to right, across the intersection with the transverse channels, including the large channels. Simple, electrokinetic material flow of the reaction mixture slugs may be accomplished by applying a voltage gradient across the length of the reaction channel, i.e. applying a first voltage to the left terminus of this channel and a second lower voltage to the right terminus of the channel, or by allowing the right terminus to float (applying no voltage). However, this type of material flow through the intersection would result in a substantial amount of diffusion at the intersections of the reaction channel and the transverse channels, resulting from both the natural diffusive properties of the material being transported in the medium used, as well as convective effects at the intersection. In controlled electrokinetic material transport, the material being transported across the intersection is constrained by applying a slight voltage gradient along the path of the material flow, e.g., from the top or bottom termini of the transverse channel, towards the right terminus of the reaction channel. This results in a "pinching" of the material flow at the intersection, which prevents the diffusion of the reaction mixture into the transverse channel. As such, the controller systems for use in conjunction with the microfluidic devices of the present invention typically include an electrical power supply and circuitry for concurrently delivering appropriate voltages to a plurality of electrodes that are placed in electrical contact with the fluids contained within these microfluidic devices. Controlled electrokinetic material transport is described in U.S. Pat. No. 5,858,195, issued Jan. 12, 1999, which is incorporated herein by reference in its entirety for all purposes. Examples of particularly preferred electrical controllers include those described in, e.g., U.S. Pat. No. 5,965,001, issued Oct. 12, 1999 and WO 98/00707, the disclosures of which are hereby incorporated herein by reference in their entirety for all purposes.

VI. Detection

The devices of the present invention may include a detection window at which signals from the reactions are monitored. The detection window typically will include a transparent cover over a channel or chamber, or transparent region of body structure allowing observation and detection of the reaction products, e.g., observation of a fluorescent response. In devices manufactured from opaque substrates, transparent detection windows fabricated from glass, quartz or a transparent polymer, may be separately manufactured into the device. However, as devices are typically fabricated from glass or transparent polymer, the optical detection window may merely be a region of a transparent cover layer, e.g. where the cover layer is glass, quartz or a transport polymer material, for e.g., PMMA polycarbonate. In devices comprising a plurality of reaction channels, the methods optionally include detecting the detectable properties in a common detection region of the plurality of parallel reaction channels using a detector in or proximal to the plurality of parallel reaction channels in the common detection region. The methods also optionally include detecting the detectable signal in each of the plurality of parallel reaction channels.

Typically, it is desired to integrate a detection step or functionality within the methods, devices and systems described herein. Detection can be based upon optical, chemical, electrochemical, thermal or other properties of reaction mixtures. In preferred aspects, detection of the signals at the detection window is achieved using an optical detection system. In the case of the fluorescent reaction products, the detector will typically include a light source which produces light at an appropriate wavelength for activating the fluorescent product, as well as optics for directing the light source through the detection window to the products contained in the channel. The light source can be any number of light sources that provides an appropriate wavelength, including lasers, laser diodes and LEDs. For example, laser activated fluorescence detection systems which employ a laser light source at an appropriate wavelength for activating the fluorescent indicator within the system may be used to monitor the fluorescence signal. Fluorescence is then detected using an appropriate detector element, e.g., a photo multiplier tube (PMT). Reaction products emitting a detectable signal can be flowed past the detector, or, alternatively, the detector can move relative to a plurality of reaction products.

VII. Method of Performing Temperature Mediated Reactions

In addition to microfluidic devices, the present invention also provides methods of using these devices for performing temperature mediated reactions. In general, temperature mediated reactions are chemical or biochemical reactions where the reactivity of one or more components is temperature dependent. Because of their flexibility, automatability, and microscale volumes, the devices described herein may be used in performing a wide variety of temperature mediated reactions, and particularly reactions where it is desirable to preheat certain reagents, e.g., Hot Start PCR.

An example of a type of temperature mediated reaction which may be run on the devices of the present invention is a thermal shift assay for ranking the affinity of a series of different molecules, i.e., ligands for a target molecule i.e., a protein which is capable of denaturing due to a thermal change. The objective is to determine whether a ligand binds to a target protein. Ligand binding has been observed to cause a shift in thermal denaturation profile of proteins. The thermal denaturation profile of the protein is measured by measuring the fluorescence of a dye noncovalently associated with the target protein. When the protein denatures, the fluorescence intensity of the dye changes. The thermal denaturation profile of the protein is measured in the absence and presence of a ligand. A shift in the mid-point temperature ($T_m$), the temperature at which the protein is 50% denatured, indicates the protein is bound to a ligand.

The method comprises contacting the target protein with a fluorescent dye. A series of ligands are introduced into the reaction channel from a sample source. The target protein and dye combination are introduced from a side channel into the reaction channel so as to coincide with the entry of a ligand. Spacer buffer plugs are also introduced into the reaction channel such that the entry of the protein-dye complex is coincident with the entry of the ligand slugs. The two different ways of measuring the thermal denaturation profile of the protein are:

i. Applying an electrical current to the heating region of the reaction channel. Measuring the denaturation of the protein-dye-ligand complex at a single temperature by measuring the fluorescence change due to protein melting as a function of time.

ii. Applying a variable electrical current to the heating region of the reaction channel and increasing the temperature within the heating current. Measuring the denaturation temperature of the protein-dye-ligand complex.

EXAMPLES

The example below is given so as to illustrate the practice of this invention. It is not intended to limit or define the entire scope of the invention.

Example 1

Ligand Induced Thermal Shift Assay

Figure 6:
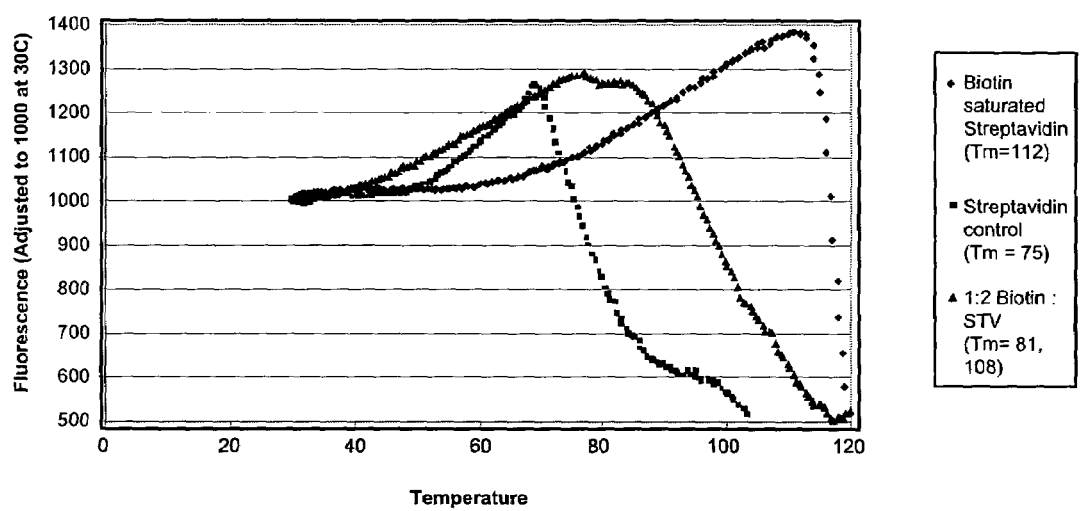
FIG. 6 illustrates ligand induced thermal shift assay on a microfluidic device.

FIG. 6 provides a ligand induced thermal shift assay showing a thermal denaturation profile for streptavidin: biotin binding at 20 mM ANS, 85 mM HEPES and 170 mM NaCl at pH 7.5.

Aqueous solutions of Streptavidin and Biotin are prepared at the following ratios: 1:0, 2:1 and 1:3. The solutions are allowed to incubate for five minutes. 1-Anilinonnapthalene-8 sulfonic acid (1,8 ANS) and HEPES buffer are added to each solution. The final concentrations of the three solutions are as follows:

1. 32 µM subunits of Streptavidin, 0 mM 1,8 ANS, 85 mM HEPES, 170 mM NaCl.
2. 32 µM subunits of Streptavidin, 16 µM subunits Biotin, 20 mM 1,8 ANS, 85 mM HEPES, 170 mM NaCl.
3. 32 µM subunits of Streptavidin, 96 µM subunits Biotin, 20 mM 1,8 ANS, 85 mM HEPES, 170 mM NaCl.

10 µL aliquots of each solution are added onto a planar microfluidic chip using pressure induced flow. The exposed solutions are covered with mineral oil to prevent evaporation. The temperature is raised at 1° C. per second using Joule heating. The change in fluorescence is monitored. (See FIG. 6).

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A method for performing a hot start polymerase chain reaction (PCR), comprising:
   loading a reaction mixture in a reaction channel of a microfluidic device, said reaction mixture comprising a primer, a template molecule, and a buffer but no polymerase enzyme;
   applying an electrical current to heat the reaction channel;
   delivering a polymerase enzyme into the reaction channel; and
   subjecting the reaction channel to conditions such that a hot start polymerase chain reaction is performed.

2. The method of claim 1, wherein the reaction mixture comprises a series of reaction mixture slugs, whereby each reaction mixture slug comprises a primer, a template molecule, and a buffer but no polymerase enzyme.

3. The method of claim 2, wherein the polymerase enzyme is delivered subsequent to the delivery of a first reaction mixture slug into the reaction channel.

4. The method of claim 1, wherein the reaction comprises denaturation of the template molecule, wherein the template molecule is denatured to provide a plurality of single stranded template molecules.

5. The method of claim 4, wherein the denaturation comprises incubation of said template molecule with a base.

6. The method of claim 1, said reaction comprising hybridization of the primer molecules to the template.

7. A method for performing a temperature mediated reaction, comprising:
   loading a first component of the temperature mediated reaction in a reaction channel of a microfluidic device;
   applying an electrical current to heat the reaction channel;
   delivering a second component of the temperature mediated reaction into the reaction channel; and
   subjecting the reaction channel to conditions such that a temperature mediated reaction is performed.

8. A method of claim 7, wherein the first component comprises a reaction mixture, said reaction mixture comprising starting materials for the temperature mediated reaction.

9. The method of claim 7, wherein the first component comprises amplification reagents for PCR comprising a template nucleic acid, a primer sequence and nucleotides.

10. The method of claim 7, wherein the second component comprises a thermally stable polymerase enzyme.

11. The method of claim 7, wherein the second component comprises DNA polymerase enzyme.

12. The method of claim 7, wherein the electrical current is an alternating current.

13. The method of claim 7, wherein said conditions include repeated cycling of a temperature within the reaction channel for carrying out denaturation, annealing and extension reactions within the temperature mediated reaction, wherein cycling the temperature comprises variably applying the electrical current.

* * * * *